US011933702B2

(12) United States Patent
Prevot et al.

(10) Patent No.: US 11,933,702 B2
(45) Date of Patent: Mar. 19, 2024

(54) APPARATUS, SYSTEM, AND METHOD FOR GAS DETECTION IN AIR DUCT SYSTEMS

(71) Applicant: Honeywell International Inc., Charlotte, NC (US)

(72) Inventors: Tanguy Prevot, Bucovic (CZ); Radovan Bakos, Rasovice (CZ); Zoltan Alexi, Brno (CZ); Jan Adamek, Brno (CZ); Duncan Gooch, Dorset (GB)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 17/805,185

(22) Filed: Jun. 2, 2022

(65) Prior Publication Data
US 2023/0393032 A1 Dec. 7, 2023

(51) Int. Cl.
*G01N 1/22* (2006.01)
*G01N 33/00* (2006.01)

(52) U.S. Cl.
CPC ....... *G01N 1/2247* (2013.01); *G01N 33/0009* (2013.01)

(58) Field of Classification Search
CPC .............. G01N 1/2247; G01N 33/0009
See application file for complete search history.

(56) References Cited

U.S. PATENT DOCUMENTS

| 6,701,772 | B2 * | 3/2004 | Kreichauf | G08B 21/12 |
| | | | | 73/23.31 |
| 9,257,027 | B2 * | 2/2016 | Williamson | G01N 1/2247 |
| 2002/0078771 | A1 | 6/2002 | Kreichauf et al. | |
| 2013/0239659 | A1 * | 9/2013 | Brighenti | G01N 21/4738 |
| | | | | 73/28.01 |

FOREIGN PATENT DOCUMENTS

| CN | 103645280 A | 3/2014 |
| CN | 107064425 A | 8/2017 |
| CN | 207439324 U | 6/2018 |
| CN | 109342653 A * | 2/2019 |

(Continued)

OTHER PUBLICATIONS

English translation of CN 109342653 accessed from iq.ip.com May 20, 2022. (Year: 2022).*

(Continued)

*Primary Examiner* — Kristina M Deherrera
*Assistant Examiner* — Jean F Morello
(74) *Attorney, Agent, or Firm* — Alston & Bird LLP

(57) ABSTRACT

Methods, apparatuses, and systems related to gas detection are provided. For example, an example apparatus for gas detection in an air duct component that receives a gas flow associated with gaseous substance is provided. The example apparatus includes a suspension connector component and a gas detection component. The suspension connector component includes a first end that is connected to a gas detection component so that the gas detection component is suspended within the air duct component. The gas detection component includes an asymmetrical outer housing so that the gas flow causes a randomized motion of the gas detection component within the air duct component.

19 Claims, 9 Drawing Sheets

(56) References Cited

FOREIGN PATENT DOCUMENTS

CN 208580082 U 3/2019

OTHER PUBLICATIONS

"Duct Smoke Detectors," Applications Guide, System Sensors, 16 pages, (2015). [Retrieved from the Internet Sep. 18, 2022: <URL: https://www.systemsensor.com/en-us/Documents/DuctSmokeDetector_Application_Guide_HVAG53.pdf>].
"DuctWatch IR Gas Detector (PIRDUCT)," Det-Tronics, (2022). [Retrieved from the Internet Sep. 18, 2022: <URL: https://www.det-tronics.com/products/ductwatch-pirduct-ir-gas-detector>].
Extended European Search Report dated Oct. 16, 2023 for EP Application No. 23173088, 9 page(s).
TFA, "Instruction Manual," 48 pages, (Oct. 17, 2014). [Retrieved from the Internet Oct. 5, 2023: URL: <https://com-tradebyte-core-tbone-media-live.s3.eu-central-1.amazonaws.com/media/1768/1800-600f2260b7b04.pdf>].

* cited by examiner

APPARATUS, SYSTEM, AND METHOD FOR GAS DETECTION IN AIR DUCT SYSTEMS

FIELD OF THE INVENTION

The present disclosure relates generally to methods, apparatuses, and systems for gas detection, and more particularly, to methods, apparatuses, and systems for detecting gaseous substances in air duct systems.

BACKGROUND

Gas detectors are electronic devices that can detect the presence of gaseous substances in an area, and/or identify the type of gaseous substances in the area. Applicant has identified many technical challenges and difficulties associated with gas detectors.

BRIEF SUMMARY

Various embodiments described herein relate to apparatuses, systems, and methods for gas detection. In particular, various embodiments are related to detecting gaseous substances in air duct systems.

In accordance with various examples of the present disclosure, an example apparatus for gas detection in an example air duct component is provided. In some embodiments, the example air duct component receives a gas flow associated with gaseous substance. In some embodiments, the example apparatus comprises a suspension connector component and a gas detection component. In some embodiments, the suspension connector component comprises a first end that is connected to the gas detection component, and the gas detection component is suspended within the air duct component. In some embodiments, the gas detection component comprises an asymmetrical outer housing so that the gas flow causes a randomized motion of the gas detection component within the air duct component.

In some embodiments, the gas detection component is suspended at a central point of the air duct component.

In some embodiments, the gas detection component is suspended at an approximately central point of the air duct component.

In some embodiments, the suspension connector component defines a suspension axis. In some embodiments, the asymmetrical outer housing of the gas detection component is asymmetrical along the suspension axis.

In some embodiments, the asymmetrical outer housing comprises a left outer housing portion and a right outer housing portion divided by the suspension axis.

In some embodiments, the right outer housing portion is larger than the left outer housing portion.

In some embodiments, the right outer housing portion comprises a handle element. In some embodiments, the left outer housing portion does not comprise the handle element.

In some embodiments, a gas detection component weight associated with the gas detection component is configured based on a flow rate of the gas flow.

In some embodiments, the asymmetrical outer housing of the gas detection component comprises a front outer housing surface and a back outer housing surface. In some embodiments, the front outer housing surface is opposite to the back outer housing surface.

In some embodiments, the front outer housing surface and the back outer housing surface are in non-parallel arrangements with a flow direction of the gas flow.

In some embodiments, the asymmetrical outer housing of the gas detection component defines at least one front flow opening on the front outer housing surface and at least one back flow opening on the back outer housing surface. In some embodiments, the gaseous substance flows through the at least one front flow opening and the at least one back flow opening.

In some embodiments, the suspension connector component comprises a second end connected to a data transmitter component that is positioned outside the air duct component.

In some embodiments, the suspension connector component comprises at least one suspension rope and at least one electrical wiring connecting the data transmitter component and the gas detection component.

In some embodiments, the at least one electrical wiring comprises at least one power cable and at least one data cable.

In some embodiments, the gas detection component is devoid of a power source.

In some embodiments, the example apparatus further comprises a connector protector component comprising a tube portion and a trumpet collar portion connected to the tube portion.

In some embodiments, the air duct component comprises an air duct wall and defines an air duct opening on the air duct wall. In some embodiments, the tube portion of the connector protector component is positioned through the air duct opening.

In some embodiments, at least a portion of the suspension connector component passes through the tube portion of the connector protector component.

In some embodiments, the trumpet collar portion of the connector protector component is positioned within the air duct component.

In some embodiments, the randomized motion of the gas detection component causes the suspension connector component to contact a trumpet collar inner surface of the trumpet collar portion without contacting an air duct inner surface of the air duct component.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1A:
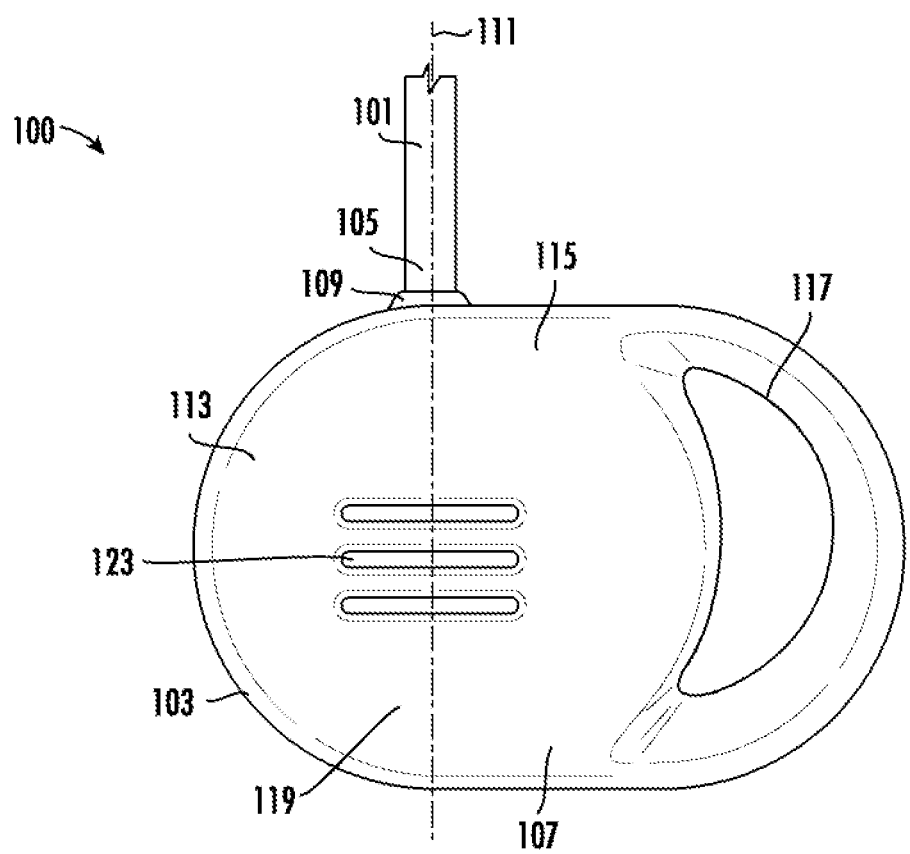
FIG. 1A illustrates an example front view of an example gas detection component and an example portion of an example suspension connector component in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The phrases "in one embodiment," "according to one embodiment," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that specific component or feature is not required to be included or to have the characteristic. Such a component or feature may be optionally included in some embodiments, or it may be excluded.

As described above, various embodiments of the present disclosure relate to the detection of gaseous substances. In particular, various embodiments of the present disclosure describe example apparatuses, systems, and methods for detecting gaseous substances in air duct components.

In the present disclosure, the term "air duct component" refers to a structure that defines one or more conduits or passages for a gas flow associated with a gaseous substance. In some embodiments, the air duct component may comprise materials such as, but not limited to, metal (such as, but not limited to, galvanized steel, aluminum, and/or the like), fiberglass, fiberboard, and/or the like. For example, an example air duct component may be formed by connecting one edge of a sheet of metal to an opposite edge of the sheet of metal, creating a hollow cylindrical or a rectangular cross section.

In some embodiments, the gaseous substance may flow through the hollow portion of the cylindrical or the rectangular cross section. Example gaseous substances may include, but are not limited to, air. In some embodiments, the air duct component may be part of a heating, ventilation, and air conditioning (HVAC) system that supplies, delivers and/or removes air in an area.

For example, an air duct component may be a part of the HVAC system in a building that is located within a petrochemical refinery. The petrochemical refinery may transfer and/or refine petroleum to other products such as gasoline, diesel fuel, asphalt base, fuel oils, heating oil, and/or the like. In this example, one or more chemicals in gaseous forms may be released into the air during the transformation and refinement process. As such, air in the air duct component may not only comprise oxygen ($O_2$) and nitrogen ($N_2$), but also likely comprise one or more of gaseous substances such as, but not limited to, hydrogen sulfide ($H_2S$), carbon monoxide (CO), carbon dioxide ($CO_2$), trioxygen ($O_3$), hydrogen ($H_2$), methane ($CH_4$), chlorine ($Cl_2$), chlorine dioxide ($ClO_2$), hydrogen cyanide (HCN), ammonia ($NH_3$), nitric oxide (NO), nitrogen dioxide ($NO_2$), phosphine ($PH_3$), sulfur dioxide ($SO_2$), and/or the like.

Continuing from the example above, air that flows in the air duct component may comprise one or more flammable or combustible gaseous substances (such as, but not limited to $H_2$, $NH_3$, and $CH_4$). In such an example, the one or more flammable or combustible gaseous substances may cause a fire or a combustion when they are mixed with the oxygen or an oxidizing agent in the air and their concentration level is between the lower explosion limit (LEL) and the upper explosion limit (UEL). As such, the presence of these gaseous substances in the air duct component can cause safety hazards.

Continuing from the example above, air that flows in the air duct component may comprise one or more gaseous substances that are harmful to the human body (such as, but not limited to, CO, HCN, and $NO_2$). Because the air duct component may be a part of an HVAC system, air from the air duct component may be released to an environment or an area where workers are present. When workers inhale the air with these harmful substances, they may become sick or develop life threatening conditions. As such, the presence of these gaseous substances can cause health hazards.

There is a need to detect the presence and/or identify the types of gaseous substances in the air that flows in the air duct component. For example, it is important to detect flammable/combustion gaseous substances from the exterior environment that may enter into the HVAC system by error. While the above example is associated with the petrochemical industry, it is noted that the scope of the present disclosure is not limited to the petrochemical industry. Other industry (such as, but not limited to, pharmaceutical industry) and/or other environments where air duct components are installed (such as, not limited to, ship vessels, off-shore platforms, and/or the like) may require the detection of and/or the identification of the types of gaseous substances in the air that flows in the air duct component.

In some examples, a gas sensor may be fixed to an air duct component. For example, steel brackets and/or mounting accessories can enable mounting or installation of the gas sensor on an inner wall of the air duct component. However, such examples do not address technical challenges and problems associated with gas detection in air duct components.

For example, one of the technical challenges and problems in such examples is that the gas sensor is not inserted deep enough into the air duct component. Because the gas sensor is mounted on the inner wall of the air duct component, the gas sensor can only sample the outer layer of the gas flow of the gaseous substance in the air duct component, creating a risk of stagnation. In contrast, the center (or the middle) of the air duct component is where the flow rate of the gaseous substance is the highest. If the air duct component is large (for example, more than 10 meters in diameter in the cross section of the air duct component), it is important to increase the amount of sampling contacts between the gas sensor and the air at different locations on the cross section of the air duct component (e.g., ideally sampling air across the entire cross section of the air duct component).

In many instances, a very short response time is needed in order for a user to be able to shut off an air duct component or stop a fan before a flammable or combustible gaseous substance enters too deep into the HVAC system. As such, it is not ideal to derive a part of the air flow in the air duct component to a detour to the gas sensor. The theoretically ideal locations of gas sensors are in the gas flow (for example, evenly distributed in several points across the cross section of the air duct component).

While duplicated gas sensors can be mounted around the air duct component to gain confidence and increase the likelihood that a gas intrusion (e.g. other gaseous substances being mixed with air as described above) can be detected, doing so can incur a high manufacturing and operation cost.

As another example, one of the technical problems is that the air duct component may not provide sufficient structural support for the gas sensor. As described above, the air duct component may comprise sheet metal, which may provide a flimsy construction. However, gas sensors and their steel brackets can be heavy. The combined weight of the gas sensors and their steel brackets can exceed the weight limit of the air duct component. This can be especially problematic on ship vessels, where vibrations can bring the air duct component into resonance and cause the air duct component to be structurally unsound.

Various embodiments of the present disclosure overcome these technical challenges and problems, and provide various technical improvements and advantages.

For example, various example embodiments of the present disclosure provide an example gas detection component that is in motion across the air duct component. For example, the gas detection component is suspended or hanged in the air duct component by a suspension connector component, and the gas flow from the air duct component may cause swinging and/or rotating motions of the gas detection component. Because of these motions, the example gas detection component can sample air from many areas among the cross section of the air duct component, and therefore providing a more representative and accurate sample of the gaseous substances that flow through the air duct component.

As another example, various example embodiments of the present disclosure provide an example gas detection system that can be easily installed on an air duct component, and can be easily maintained. For example, the example gas detection system comprises an example gas detection component that can be easily removed from the air duct component for cleaning and servicing. In contrast, many solutions rely on brackets and bolts to affix a gas sensor to an air duct component, increasing the difficulties in installation and maintenance. Various embodiments of the present disclosure provide a simplified gas detection component that can reduce the weight burden exerted on the air duct component.

Figure 1B:
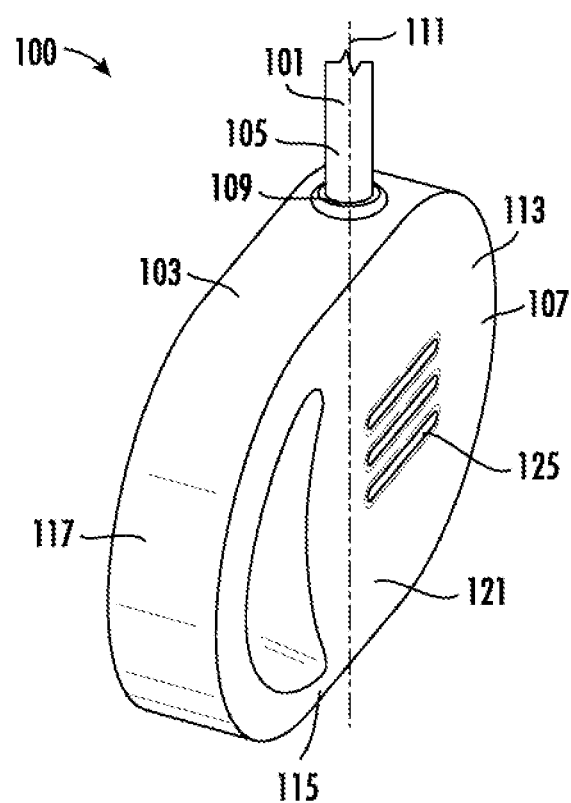
FIG. 1B illustrates an example angled view of the example gas detection component and the example portion of the example suspension connector component shown in FIG. 1A in accordance with various embodiments of the present disclosure.
Figure 1C:
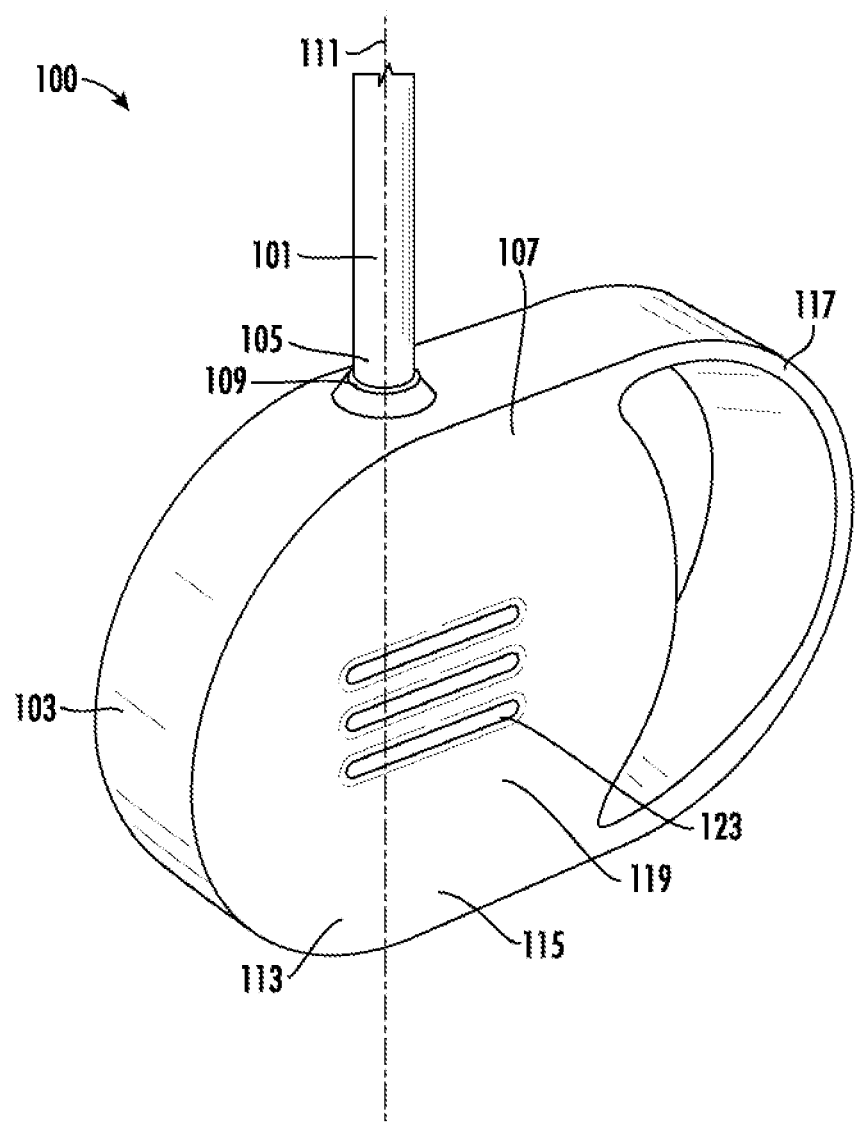
FIG. 1C illustrates another example angled view of the example gas detection component and the example portion of the example suspension connector component shown in FIG. 1A in accordance with various embodiments of the present disclosure.

Referring now to FIG. 1A, FIG. 1B, and FIG. 1C, example views illustrate example portions of an example apparatus 100 for gas detection in an air duct component that receives a gas flow associated with gaseous substance (e.g. the gas flow comprises the gaseous substance) in accordance with some embodiments of the present disclosure. As shown in FIG. 1A, FIG. 1B, and FIG. 1C, the example apparatus 100 comprises an example gas detection component 103 and an example suspension connector component 101.

In particular, FIG. 1A illustrates an example front view of the example gas detection component 103 and the example portion of the example suspension connector component 101. FIG. 1B illustrates an example angled view of the example gas detection component 103 and the example portion of the example suspension connector component 101. FIG. 1C illustrates another example angled view of the example gas detection component 103 and the example portion of the example suspension connector component 101.

In some embodiments, the suspension connector component 101 comprises a first end 105 that is connected to the gas detection component 103. In some embodiments, the suspension connector component 101 may comprise at least one suspension rope and at least one electrical wiring. For example, the suspension connector component 101 illustrated in FIG. 1A to FIG. 1C is a combination of at least one suspension rope and at least one electrical wiring. In some embodiments, both a first end of at least one suspension rope and a first end of the at least one electrical wiring are connected to the gas detection component 103.

In some embodiments, the at least one suspension rope may comprise material(s) that have a high breaking tenacity. For example, the at least one suspension rope may comprise materials such as, but not limited to, high strength yarn material (e.g. spectra fiber). As such, the suspension connector component 101 is durable despite the constant pendulum motion of the gas detection component 103 in the turbulent air flow within the air duct component and provides various technical benefits and advantages, details of which are described herein.

Additionally, or alternatively, the at least one suspension rope may comprise material(s) that are flame resistant. For example, the at least one suspension rope may comprise materials such as, but not limited to, glass fiber. As such, the suspension connector component 101 provides technical benefits and advantages such as, but not limited to, preventing the gas detection component 103 from being disconnected in the event of fire or combustion.

While the description above provides example materials of the at least one suspension rope of the suspension connector component 101, it is noted that the scope of the present disclosure is not limited to the description above. In some examples, an example suspension rope of the suspension connector component 101 may comprise one or more additional and/or alternative materials.

In some embodiments, the at least one electrical wiring of the suspension connector component 101 may be positioned within and/or in parallel with the at least one suspension rope of suspension connector component 101. In some embodiments, the at least one electrical wiring may comprise material such as, but not limited to, copper. In some embodiments, the at least one electrical wiring may be connected through an intrinsically safe barrier that limits the voltage or current. In some embodiments, the at least one electrical wiring comprises two wires that are loop powered and through an intrinsically safe barrier.

In some embodiments, the at least one electrical wiring may comprise at least one power cable for conveying power to the gas detection component 103 and at least data cable for enabling data communications between the gas detection component 103 and a data transmitter component, details of which are illustrated and described in connection with at least FIG. 3A to FIG. 3C.

In the example shown in FIG. 1A, the gas detection component 103 comprises an asymmetrical outer housing 107. In some embodiments, the first end 105 of the suspension connector component 101 is secured to the asymmetrical outer housing 107 of the gas detection component 103. For example, the first end of the at least one suspension rope of the suspension connector component 101 is secured to a connecting portion 109 that is on the top surface of the asymmetrical outer housing 107 of the gas detection component 103, as shown in FIG. 1A. In some embodiments, the connecting portion 109 provides an intrinsically safe barrier between the gas detection component 103 and the suspension connector component 101. In some embodiments, the intrinsically safe barrier limits the voltage and/or the current from the gas detection component 103 to the suspension connector component 101 and/or from the suspension connector component 101 to the gas detection component 103.

In some embodiments, the asymmetrical outer housing 107 may comprise material(s) such as, but not limited to, plastic (e.g. polyvinyl chloride, polycarbonate, and/or the like). In some embodiments, the asymmetrical outer housing 107 of the gas detection component 103 may provide a housing for one or more gas sensors. In other words, one or more gas sensors are positioned within the asymmetrical outer housing 107.

For example, the gas detection component 103 may comprise a $H_2S$ sensor. In such an example, the gas detection component 103 can detect and/or identify the presence of $H_2S$ gaseous substance (for example, in the gas flow of an air duct component as described herein). Additionally, or alternatively, the gas detection component 103 may comprise a CO sensor. In such an example, the gas detection component 103 can detect and/or identify the presence of CO gaseous substance (for example, in the gas flow of an air duct component as described herein). Additionally, or alternatively, the gas detection component 103 may comprise a $CO_2$ sensor. In such an example, the gas detection component 103 can detect and/or identify the presence of $CO_2$ gaseous substance (for example, in the gas flow of an air duct component as described herein). Additionally, or alternatively, the gas detection component 103 may comprise an $O_3$ sensor. In such an example, the gas detection component 103 can detect and/or identify the presence of $O_3$ gaseous substance (for example, in the gas flow of an air duct component as described herein). Additionally, or alternatively, the gas detection component 103 may comprise an $H_2$ sensor. In such an example, the gas detection component 103 can detect and/or identify the presence of $H_2$ gaseous substance (for example, in the gas flow of an air duct component as described herein). Additionally, or alternatively, the gas detection component 103 may comprise a $CH_4$ sensor. In such an example, the gas detection component 103 can detect and/or identify the presence of $CH_4$ gaseous substance (for example, in the gas flow of an air duct component as described herein). Additionally, or alternatively, the gas detection component 103 may comprise a $Cl_2$ sensor. In such an example, the gas detection component 103 can detect and/or identify the presence of $Cl_2$ gaseous substance (for example, in the gas flow of an air duct component as described herein). Additionally, or alternatively, the gas detection component 103 may comprise a $ClO_2$ sensor. In such an example, the gas detection component 103 can detect and/or identify the presence of $ClO_2$ gaseous substance (for example, in the gas flow of an air duct component as described herein). Additionally, or alternatively, the gas detection component 103 may comprise a HCN sensor. In such an example, the gas detection component 103 can detect and/or identify the presence of HCN gaseous substance (for example, in the gas flow of an air duct component as described herein). Additionally, or alternatively, the gas detection component 103 may comprise an $NH_3$ sensor. In such an example, the gas detection component 103 can detect and/or identify the presence of $NH_3$ gaseous substance (for example, in the gas flow of an air duct component as described herein). Additionally, or alternatively, the gas detection component 103 may comprise a NO sensor. In such an example, the gas detection component 103 can detect and/or identify the presence of NO gaseous substance (for example, in the gas flow of an air duct component as described herein). Additionally, or alternatively, the gas detection component 103 may comprise a $NO_2$ sensor. In such an example, the gas detection component 103 can detect and/or identify the presence of $NO_2$ gaseous substance (for example, in the gas flow of an air duct component as described herein). Additionally, or alternatively, the gas detection component 103 may comprise a $PH_3$ sensor. In such an example, the gas detection component 103 can detect and/or identify the presence of $PH_3$ gaseous substance (for example, in the gas flow of an air duct component as described herein). Additionally, or alternatively, the gas detection component 103 may comprise a $SO_2$ sensor. In such an example, the gas detection component 103 can detect and/or identify the presence of $SO_2$ gaseous substance (for example, in the gas flow of an air duct component as described herein).

While the description above provides examples of gas sensors that can be positioned within the asymmetrical outer housing 107 of the gas detection component 103, it is noted that the scope of the present disclosure is not limited to the description above. In some examples, an example gas detection component may comprise one or more additional and/or alternative gas sensors.

As described above, the suspension connector component 101 may comprise at least one electrical wiring that includes, but not limited to, at least one power cable and at least one data cable. In some embodiments, the one or more gas sensors that are positioned with the asymmetrical outer housing 107 of the gas detection component 103 are connected to the at least one electrical wiring. For example, the one or more gas sensors are connected to the at least one power cable of the at least one electrical wiring and receives electrical power. Additionally, or alternatively, the one or more gas sensors are connected to the at least one data cable of the at least one electrical wiring and transfer data (for example, detection signals) through the at least one data cable. Additional example details are described in connection with at least FIG. 3A to FIG. 3C.

In some embodiments, the asymmetrical outer housing 107 of the gas detection component 103 defines one or more flow openings on one or more outer housing surfaces of the asymmetrical outer housing 107. In such an example, the one or more flow openings may be in the form of gaps, apertures, orifices, and/or the like so that gaseous substance can flow from outside the asymmetrical outer housing 107 of the gas detection component 103 to inside the asymmetrical outer housing 107 of the gas detection component 103, and/or flow from inside the asymmetrical outer housing 107 of the gas detection component 103 to outside the asymmetrical outer housing 107 of the gas detection component 103. As such, the one or more gas sensors within the asymmetrical outer housing 107 of the gas detection component 103 can detect and/or identify the presence of various gaseous substances (for example, in the gas flow of an air duct component as described herein).

For example, the asymmetrical outer housing 107 of the gas detection component 103 comprises a front outer housing surface 119 and a back outer housing surface 121 as shown in FIG. 1A and FIG. 1B. In some embodiments, the front outer housing surface 119 is opposite to the back outer housing surface 121. For example, the front outer housing surface 119 may correspond to a front portion of the asymmetrical outer housing 107 where the gaseous substances may flow onto. The back outer housing surface 121 may correspond to a back portion of the asymmetrical outer housing 107 where the gaseous substances may flow from. In some embodiments, the gas flow of the gaseous substance in the air duct component 507 pushes the front outer housing surface 119 of the asymmetrical outer housing 107.

In the example shown in FIG. 1A to FIG. 1C, the asymmetrical outer housing 107 of the gas detection component 103 defines at least one front flow opening 123 on the front outer housing surface 119 and at least one back flow opening 125 on the back outer housing surface 121. In some embodiments, the gaseous substance flows through the at least one front flow opening 123 and the at least one back flow opening 125. For example, the gaseous substance may flow into the asymmetrical outer housing 107 of the gas detection component 103 through the at least one front flow opening 123, and may flow out of the asymmetrical outer housing 107 of the gas detection component 103 through the at least one back flow opening 125. In some embodiments, when the gaseous substance flows within asymmetrical outer housing 107 of the gas detection component 103, the one or more gas sensors that are positioned within the asymmetrical outer housing 107 may detect and/or identify the presence of various gaseous substances, and may generate detection signals.

While the description above provides example contacts between the air flow and the front outer housing surface (or between the air flow and the back outer housing surface), it is noted that the scope of the present disclosure is not limited to the description above. For example, the air flow may cause the gas detection component 103 to rotate, to move, to swinging, and/or the like.

In some embodiments, the front outer housing surface 119 and the back outer housing surface 121 are in non-parallel arrangements with a flow direction of the gas flow. For example, the front outer housing surface 119 may be at an angle with the flow direction of the gas flow that is not at 0 degrees and is not at 180 degrees. Similarly, the back outer housing surface 121 may be at an angle with the flow direction of the gas flow that is not at 0 degrees and is not at 180 degrees. Such example arrangements provide technical benefits such as, but not limited to, enabling the gaseous substance in the gas flow to flow into the asymmetrical outer housing 107 of the gas detection component 103 (for example, through the at least one front flow opening 123 on the front outer housing surface 119 described above) and flow out of the asymmetrical outer housing 107 of the gas detection component 103 (for example, through the at least one back flow opening 125 on the back outer housing surface 121 described above). In addition, the non-parallel arrangements also enable the gas flow to push the outer surfaces of the asymmetrical outer housing 107 of the gas detection component 103, therefore causing a randomized motion of the gas detection component 103.

For example, as illustrated in FIG. 1A to FIG. 1C, the asymmetrical outer housing 107 of the gas detection component 103 is in an asymmetrical shape. In some embodiments, the asymmetrical shape of the asymmetrical outer housing 107 of the gas detection component 103 provides various technical benefits and advantages, and overcomes various technical challenges and difficulties associated with gas detection in air duct components.

As described above, the gas detection component 103 may be suspended within an air duct component through the suspension connector component 101 (e.g., similar to a pendulum). In some embodiments, the air duct component receives a gas flow associated with one or more gaseous substances. In some embodiments, the gas detection component 103 is immersed in the gas flow and exposed to the gaseous substance. In some embodiments, the gaseous substance from the gas flow exerts aerodynamic force on the surface of the asymmetrical outer housing 107 of the gas detection component 103. Because the asymmetrical outer housing 107 is in an asymmetrical shape, the force exerted on different portions of the asymmetrical outer housing 107 by the gas flow are different, therefore creating asymmetrical aerodynamic forces on the asymmetrical outer housing 107. Because the gas detection component 103 is suspended within the air duct component through the suspension connector component 101, the asymmetrical aerodynamic forces cause a randomized motion of the gas detection component 103. As such, the asymmetrical outer housing 107 of the gas detection component 103 enables the gas flow within the air duct component to exert aerodynamic forces on the gas detection component 103 and causes the randomized motion of the gas detection component 103 within the air duct component, therefore maintaining motion and swinging of the gas detection component 103 even in a constant flow of gaseous substance. Examples of the randomized motion may include, but are not limited to, a left movement motion, a right movement motion, a front movement motion, a back movement motion, an up movement motion, a down movement motion, a rotating motion, a swinging motion, and/or the like.

In accordance with various embodiments of the present disclosure, the asymmetrical shape of the asymmetrical outer housing 107 provides various technical benefits and advantages. For example, one of the technical challenges and difficulties associated with gas detection in air duct components described above is the lack of sufficient sampling contact with the gaseous substance in the gas flow. Because of the randomized motion of the gas detection component 103 within the air duct component that is caused by the asymmetrical shape of the asymmetrical outer housing 107, the gas detection component 103 may sample gaseous substances in different locations on the cross section of the air duct component. Therefore, the asymmetrical shape of the asymmetrical outer housing 107 enables various embodiments of the present disclosure to increase the sampling contacts of the gas sensors and the gaseous substance, and provide more accurate detection results of gaseous substance in the air duct component.

Additionally, the randomized motion of the gas detection component 103 is caused and energized by the gas flow within the air duct component. As such, various embodiments of the present disclosure can increase sampling contacts of gas sensors and gaseous substance without requiring duplicated gas sensors, therefore providing technical benefits such as, but not limited to, reducing the weight that is imposed on the air duct component by the gas detection component, reducing manufacturing and operation cost, and increasing the easiness and the simplicity in installing and maintaining the gas detection systems.

In the example shown in FIG. 1A to FIG. 1C, the suspension connector component 101 defines a suspension axis 111. In such an example, the suspension axis 111 refers to a central axis of the suspension connector component 101. In some embodiments, the asymmetrical outer housing 107 of the gas detection component 103 is asymmetrical along the suspension axis 111.

For example, the asymmetrical outer housing 107 comprises a left outer housing portion 113 and a right outer housing portion 115 divided by the suspension axis 111 as shown in FIG. 1A to FIG. 1C. In some embodiments, the right outer housing portion 115 is larger than the left outer housing portion 113. For example, the asymmetrical outer housing 107 of the gas detection component 103 may be in contact with a gas flow and exposed to gaseous substance in an air duct component. In some embodiments, the surface area of the right outer housing portion 115 that is in contact with the gaseous substance in the gas flow is larger than the surface area of the left outer housing portion 113 that is in contact with the gaseous substance in the gas flow. In some embodiments, the size difference between the right outer housing portion 115 of the asymmetrical outer housing 107 and the left outer housing portion 113 of the asymmetrical outer housing 107 causes the gaseous substance in the gas flow to exert asymmetrical aerodynamic forces on the gas detection components, therefore creating a randomized motion of the gas detection component 103 and providing various technical benefits and advantages as described above.

Additionally, or alternatively, the right outer housing portion 115 comprises a handle element 117. For example, a top end of handle element 117 is connected to a top portion of the right outer housing portion 115, and a bottom end of the handle element 117 is connected to a bottom portion of the right outer housing portion 115. The left outer housing portion does not comprise the handle element 117. As such, the surface area of the right outer housing portion 115 that is in contact with the gaseous substance in the gas flow is different from the surface area of the left outer housing portion 113 that is in contact with the gaseous substance in the gas flow, causing the gaseous substance in the gas flow to exert asymmetrical aerodynamic forces on the gas detection components and creating a randomized motion of the gas detection component 103, providing various technical benefits and advantages as described above.

Figure 2:
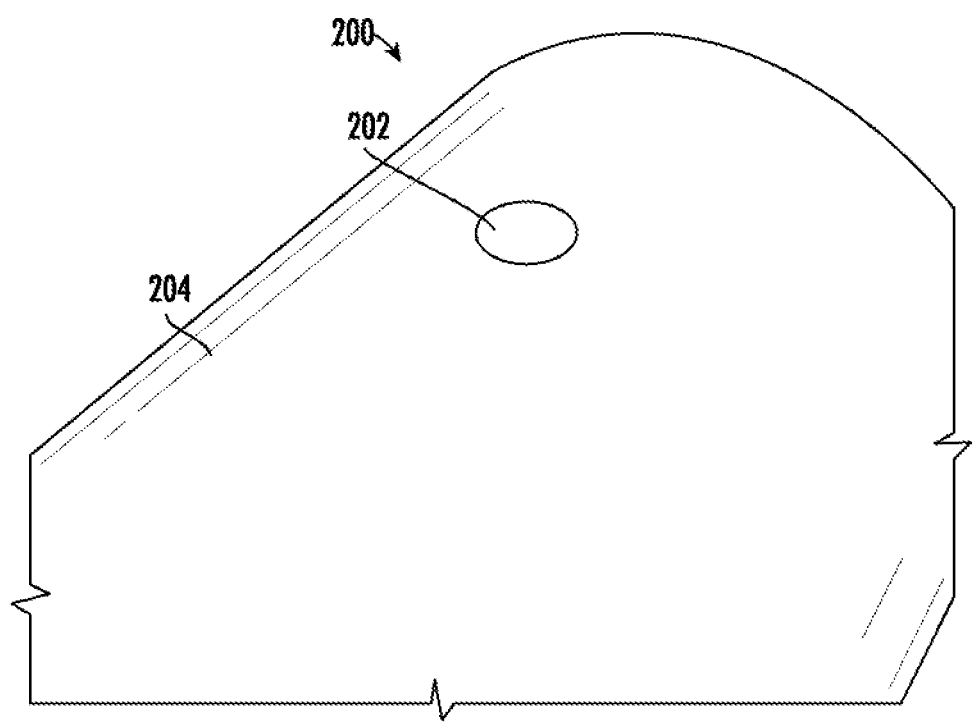
FIG. 2 illustrates an example view of an example air duct component in accordance with some embodiments of the present disclosure.

Referring now to FIG. 2, an example view of an example air duct component 200 in accordance with some embodiments of the present disclosure is illustrated.

Similar to those described above, the example air duct component 200 defines one or more conduits or passages for a gas flow associated with a gaseous substance. In some embodiments, the example air duct component 200 may comprise material(s) such as, but not limited to, metal (such as, but not limited to, galvanized steel, aluminum, and/or the like), fiberglass, fiberboard, and/or the like.

For example, the example air duct component 200 may comprise an air duct wall 204 that is formed by connecting one edge of a sheet of metal to an opposite edge of the sheet of metal, creating a hollow cylindrical cross section. In the example shown in FIG. 2, the example air duct component 200 defines an air duct opening 202 on the air duct wall 204.

In some embodiments, the air duct opening 202 on the air duct wall 204 may be formed through manufacturing techniques such as, but not limited to, machine cutting. In some embodiments, a size of the air duct opening 202 may be determined based on a size of a gas detection component and a size of a suspension connector component in accordance with some embodiments of the present disclosure. For example, the size of the air duct opening 202 is large enough to allow the gas detection component and the suspension connector component to pass through.

As described above, an example gas detection component in accordance with some embodiments of the present disclosure is connected to an example suspension connector component. As such, an example manufacturing/assembling method in accordance with some embodiments of the present disclosure comprises cutting the air duct wall 204 of the air duct component 200 to form the air duct opening 202, positioning a gas detection component through the air duct opening 202, and suspending/hanging the gas detection component within the air duct component 200 via a suspension connector component. In some embodiments, the suspension connector component passes through a connector protector component, and the connector protector component is positioned through the air duct opening 202 on the air duct wall 204 of the air duct component 200, so that at least a part of the connector protector component is positioned within the air duct component 200 and a part of the connector protector component is positioned outside the air duct component 200. Additional details are described in connection with at least FIG. 3A to FIG. 3B.

Figure 3A:
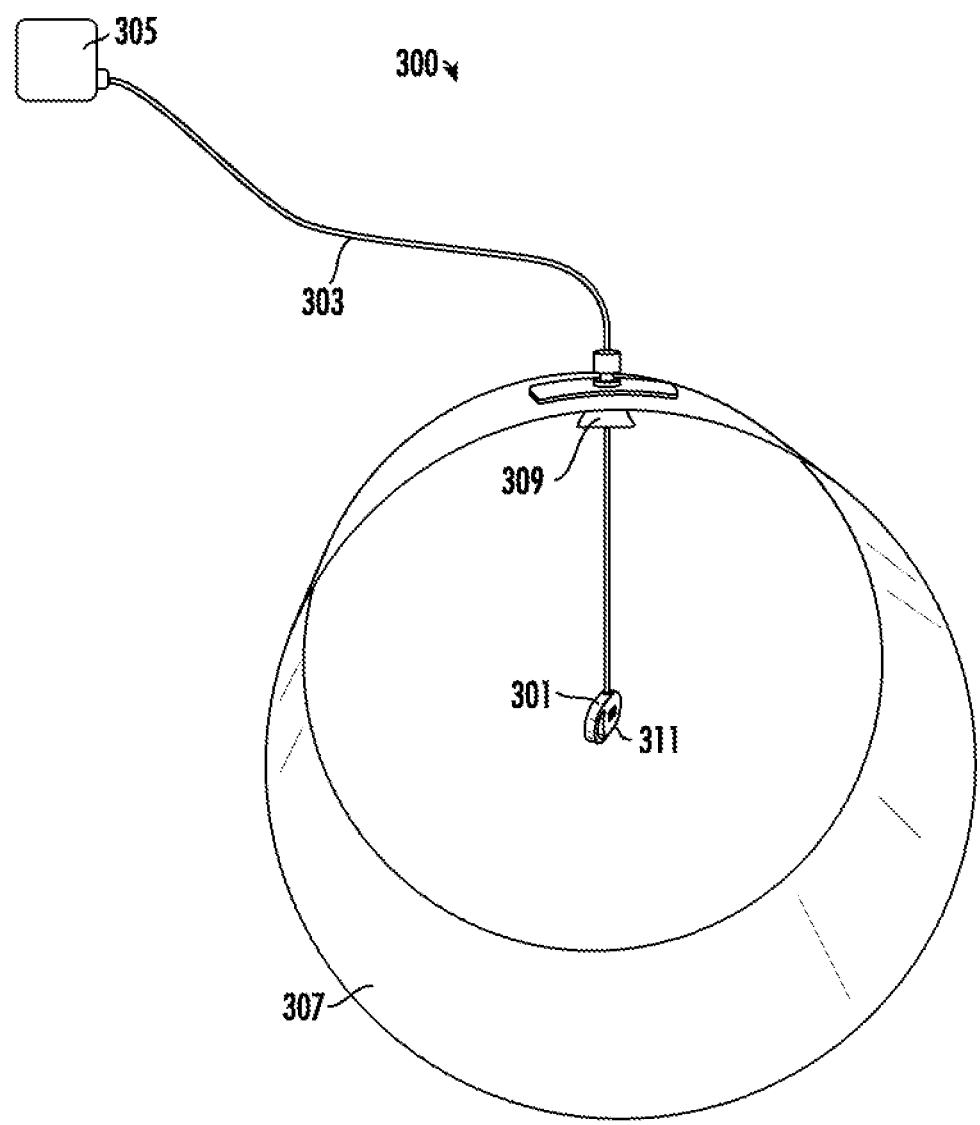
FIG. 3A illustrates an example gas detection system that comprises an example gas detection component, an example suspension connector component, and an example data transmitter component in accordance with some embodiments of the present disclosure.
Figure 3B:
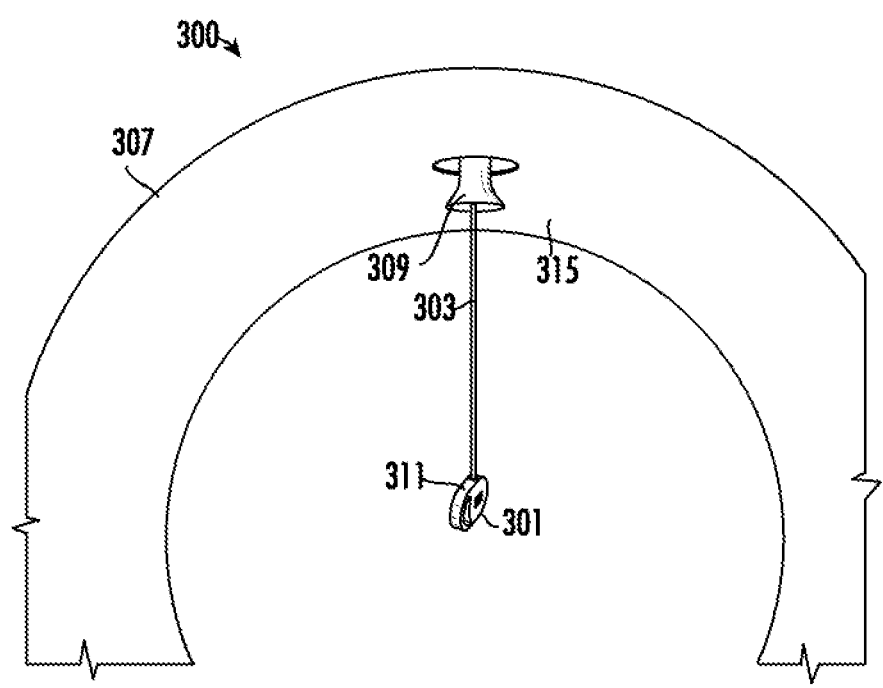
FIG. 3B illustrates an example view of a portion of an example air duct component and the example gas detection component shown in FIG. 3A in accordance with some embodiments of the present disclosure.
Figure 3C:
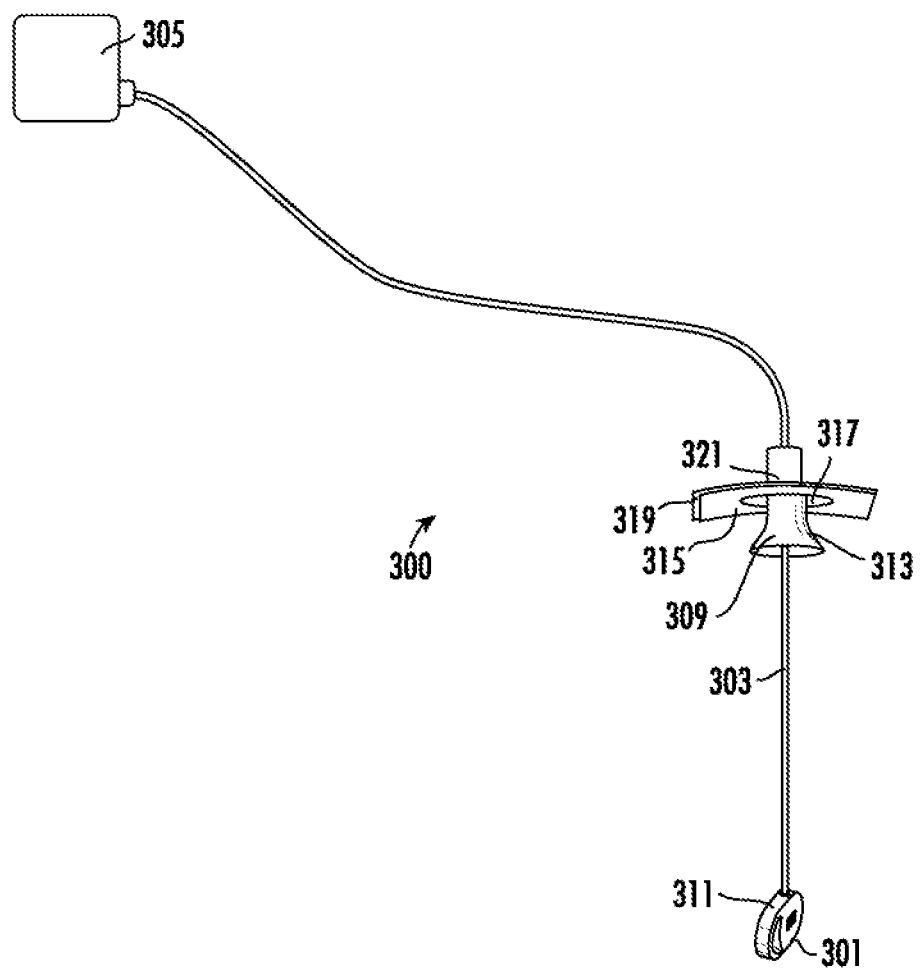
FIG. 3C illustrates an example view of the example data transmitter component and the example gas detection component that are connected through the example suspension connector component shown in FIG. 3A in accordance with some embodiments of the present disclosure.

Referring now to FIG. 3A, FIG. 3B, and FIG. 3C, example views associated with example portions of an example gas detection system 300 in accordance with some embodiments of the present disclosure are provided. As shown in FIG. 3A, FIG. 3B, and FIG. 3C, the example gas detection system 300 comprises an example gas detection component 301, an example data transmitter component 305, and an example suspension connector component 303.

In particular, FIG. 3A illustrates the example suspension connector component 303 connecting the example gas detection component 301 and the example data transmitter component 305 of the example gas detection system 300. FIG. 3B illustrates an example view of a portion of the example air duct component 307 and the example gas detection component 301. FIG. 3C illustrates an example view of the example gas detection system 300 without the example air duct component 307.

As illustrated in the example shown in FIG. 3A, the suspension connector component 303 comprises a first end that is connected to the gas detection component 301 (which is suspended within an air duct component 307) and a second end connected to the data transmitter component 305 (which is positioned outside the air duct component 307). In some embodiments, the suspension connector component 303 comprises at least one suspension rope and at least one electrical wiring connecting the data transmitter component 305 and the gas detection component 301.

In some embodiments, the at least one suspension rope may comprise a first end that is connected to the asymmetrical outer housing 311 of the example gas detection component 301, and a second end that is connected to a housing of the data transmitter component 305. In some embodiments, the data transmitter component 305 is securely positioned and immovable. For example, the data transmitter component 305 may be fixed or mounted on a wall. As such, the at least one suspension rope of the suspension connector component 303 provides structural support that enables the gas detection component 301 to be suspended within the air duct component 307 (similar to a pendulum). In some embodiments, the air duct component 307 receives a gas flow associated with gaseous substance.

Similar to those described above in connection with FIG. 1A to FIG. 1C, the at least one suspension rope may comprise material(s) that have a high breaking tenacity. For example, the at least one suspension rope may comprise materials such as, but not limited to, high strength yarn material (e.g. spectra fiber). As such, the suspension connector component 303 is durable despite the constant pendulum motion of the gas detection component 301 in the turbulent air flow within the air duct component, therefore providing various technical benefits and advantages, details of which are described herein.

Additionally, or alternatively, the at least one suspension rope may comprise material(s) that are flame resistant. For example, the at least one suspension rope may comprise materials such as, but not limited to, glass fiber. As such, the suspension connector component 303 provides technical benefits and advantages such as, but not limited to, preventing the gas detection component 301 from being disconnected in the event of fire or combustion.

While the description above provides example materials of the at least one suspension rope of the suspension connector component 303, it is noted that the scope of the present disclosure is not limited to the description above. In some examples, an example suspension rope of the suspension connector component 303 may comprise one or more additional and/or alternative materials.

In some embodiments, the at least one electrical wiring of the suspension connector component 303 may be positioned within or in parallel with the at least one suspension rope of suspension connector component 303. In some embodiments, the at least one electrical wiring may comprise material(s) such as, but not limited to, copper. Additionally, or alternatively, the at least one electrical wiring may comprise other material(s).

In some embodiments, the at least one electrical wiring may comprise at least one power cable for conveying power to the gas detection component 301 and at least one data cable for enabling data communications between the gas detection component 301 and the data transmitter component 305.

For example, the data transmitter component 305 may comprise a power source (such as, but not limited to, a battery). Similar to those described above, the gas detection component 301 comprises one or more gas sensors that require electrical power to operate. In some embodiments, the power cable of the at least one electrical wiring connects the power source of the data transmitter component 305 to the one or more gas sensors of the gas detection component 301, therefore providing power to the gas detection component 301. As such, the gas detection component 301 itself is devoid of a power source (for example, there is no battery in the gas detection component 301), providing technical benefits and advantages such as, but not limited to, reducing the weight of the gas detection component 301. Additionally, the gas detection component 301 may also be in contact with a flammable or combustible gaseous substance in the air duct component. As such, removing the power source from the gas detection component 301 also allows the gas detection component 301 to satisfy safety requirements.

Additionally, or alternatively, the data transmitter component 305 may comprise one or more signal processing circuitries (for example, but not limited to, one or more analog to digital converter (ADC) circuits, signal amplifying circuits, and/or the like). As described above, the one or more gas sensors within the gas detection component 301 may generate gas detection signals. In some embodiments, the data cable of the at least one electrical wiring connects the one or more gas sensors to the one or more signal processing circuitries of the data transmitter component 305. As such, the data transmitter component 305 may receive gas detection signals from the gas detection component 301 via the data cable of the at least one electrical wiring.

While the description above illustrates example elements of the data transmitter component 305, it is noted that the scope of the present disclosure is not limited to the description above. In some examples, an example data transmitter component may comprise one or more additional and/or alternative elements.

In particular, the at least one electrical wiring of the suspension connector component 303 enables power supply and data communications between the gas detection component 301 and the data transmitter component 305. As such, various embodiments of the present disclosure reduce the weight of the gas detection component 301 by positioning various elements in the data transmitter component 305 instead of in the gas detection component 301, providing the technical benefits and advantages of enabling gas detection in air duct components that have low weight bearing limits.

Additionally, the gaseous substance in the air duct component may comprise flammable or combustible gaseous substances. As such, the gas detection component 301 should be intrinsically safe in that the gas detection component 301 should be devoid of any components that can produce energy to cause ignition of the flammable or combustible gaseous substance. As such, the gas detection component 301 may be devoid of a battery, devoid of a Bluetooth module, devoid of a display, and/or the like, providing the technical benefits and advantages of satisfying safety requirements.

For example, the data transmitter component 305 comprises one or more processing circuities, and the gas detection component 301 is devoid of any processing circuities. In accordance with various embodiments of the present disclosure, the processing circuities of the data transmitter component 305 may be embodied in a number of different ways. For example, the processing circuities may be embodied as one or more complex programmable logic devices (CPLDs), microprocessors, multi-core processors, co-processing entities, application-specific instruction-set processors (ASIPs), and/or controllers. Further, the processing circuities may be embodied as one or more other processing devices or circuitry. The term circuitry may refer to an entirely hardware embodiment or a combination of hardware and computer program products. Thus, the processing circuities may be embodied as integrated circuits, application specific integrated circuits (ASICs), field programmable gate arrays (FPGAs), programmable logic arrays (PLAs), hardware accelerators, another circuitry, and/or the like.

Additionally, or alternatively, the data transmitter component 305 comprises one or more data transmission circuits, and the gas detection component 301 is devoid of any data transmission circuits. In some embodiments, the one or more data transmission circuits of the data transmitter component 305 enable the data transmitter component 305 to communicate with various computing entities, such as by communicating data, content, information, and/or similar terms used herein interchangeably that can be transmitted, received, operated on, processed, displayed, stored, and/or the like. For example, the data transmitter component 305 may transmit detection signals received from the gas detection component 301 to one or more other computing systems (such as the customer's systems or a safety suite). Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data transmitter component 305 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The data transmitter component 305 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/ Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

Additionally, or alternatively, the data transmitter component 305 comprises one or more display circuities, and the gas detection component 301 is devoid of any display circuities.

Referring now to FIG. 3B, the gas detection component 301 is suspended at a central point of the air duct component 307. In some embodiments, the central point of the air duct component 307 corresponds to a central axis of the gas flow of the gaseous substance in the air duct component. In some embodiments, the gas detection component 301 is suspended at the approximately central point of the air duct component 307.

For example, the length of the suspension connector component 303 (for example, including the at least one suspension rope and the at least one electrical wiring) can be customized according to the size of the air duct component 307, so that the nominal position of the gas detection component 301 is as close as possible to the central portion of the cross section of the air duct component. For example, if the diameter of the air duct component 307 is 3 meters, then the length of the suspension connector component 303 from the air duct wall of the air duct component 307 to the gas detection component 301 is 1.5 meters.

As described above, the central point of the air duct component 307 is where the flow rate of the gaseous substance is the highest. As such, by suspending or hanging the gas detection component 301 at the central point or at an approximately central point of the air duct component 307, the gas detection component 301 can utilize the motion of the gas flow to obtain a more relevant sample of the air in the air duct component 307 so as to detect gaseous substance, therefore providing various technical benefits and advantages such as, but not limited to, increasing sampling contact between gas detection component 301 and the gaseous substance in the gas flow.

Similar to those described above in connection with at least FIG. 1A to FIG. 1C, the gas detection component 301 comprises an asymmetrical outer housing 311.

In some embodiments, the asymmetrical outer housing 311 may comprise material such as, but not limited to, plastic (e.g. polyvinyl chloride, polycarbonate, and/or the like). In some embodiments, the asymmetrical outer housing of the gas detection component 301 may provide a housing for one or more gas sensors. Examples of gas sensors that are positioned within the asymmetrical outer housing 311 of the gas detection component 301 may include, but are not limited to, one or more of $H_2S$ sensors, CO sensors, $CO_2$ sensors, $O_3$ sensors, $H_2$ sensors, $CH_4$ sensors, $Cl_2$ sensors, $ClO_2$ sensors, HCN sensors, $NH_3$ sensors, NO sensors, $NO_2$ sensors, $PH_3$ sensors, $SO_2$ sensors, and/or the like.

Similar to those described above in connection with at least FIG. 1A to FIG. 1C, the asymmetrical outer housing 311 of the gas detection component 301 defines one or more flow openings on one or more outer housing surfaces of the asymmetrical outer housing 311 of the gas detection component 301. In such an example, the one or more flow openings may be in the form of gaps, apertures, orifices, and/or the like so that gaseous substance can flow from outside the asymmetrical outer housing 311 of the gas detection component 301 to inside the asymmetrical outer housing 311 of the gas detection component 301, and/or flow from inside the asymmetrical outer housing 311 of the gas detection component 301 to outside the asymmetrical outer housing 311 of the gas detection component 301. As such, the one or more gas sensors within the asymmetrical outer housing 311 of the gas detection component 301 can detect and/or identify the presence of various gaseous substances (for example, in the gas flow of the air duct component 307).

Similar to those described above in connection with at least FIG. 1A to FIG. 1C, the asymmetrical outer housing 311 of the gas detection component 301 comprises a front outer housing surface and a back outer housing surface. In some embodiments, the front outer housing surface is opposite to the back outer housing surface. For example, the front outer housing surface may correspond to a front portion of the asymmetrical outer housing 311 where the gaseous substances may flow onto. The back outer housing surface may correspond to a back portion of the asymmetrical outer housing 311 where the gaseous substances may flow from.

Similar to those described above in connection with at least FIG. 1A to FIG. 1C, the asymmetrical outer housing 311 of the gas detection component 301 defines at least one front flow opening on the front outer housing surface and at least one back flow opening on the back outer housing surface. In some embodiments, the gaseous substance flows through the at least one front flow opening and the at least one back flow opening. For example, the gaseous substance may flow into the asymmetrical outer housing 311 of the gas detection component 301 through the at least one front flow opening, and may flow out of the asymmetrical outer housing 311 of the gas detection component 301 through the at least one back flow opening. In some embodiments, when the gaseous substance flows within asymmetrical outer housing 311 of the gas detection component 301, the one or more gas sensors that are positioned within the asymmetrical outer housing 311 may detect and/or identify the presence of various gaseous substances, and may generate detection signals.

Similar to those described above in connection with at least FIG. 1A to FIG. 1C, the front outer housing surface and the back outer housing surface are in non-parallel arrangements with a flow direction of the gas flow. For example, the front outer housing surface may be at an angle with the flow direction of the gas flow that is not at 0 degrees and is not at 180 degrees. Similarly, the back outer housing surface may be at an angle with the flow direction of the gas flow that is not at 0 degrees and is not at 180 degrees. Such example arrangements provide the technical benefits of enabling the gaseous substance in the gas flow to flow into the asymmetrical outer housing 311 of the gas detection component 301 (for example, through the front flow opening on the front outer housing surface described above) and flow out of the asymmetrical outer housing 311 of the gas detection component 301 (for example, through the back flow opening on the back outer housing surface described above).

Similar to those described above in connection with at least FIG. 1A to FIG. 1C, the asymmetrical outer housing 311 of the gas detection component 301 is in an asymmetrical shape. In some embodiments, the asymmetrical shape of the asymmetrical outer housing of the gas detection component 301 provides various technical benefits and advantages, and overcomes various technical challenges and difficulties associated with gas detection in air duct components. For example, the asymmetrical outer housing 311 of the gas detection component 301 enables the gas flow within the air duct component 307 to cause a randomized motion of the gas detection component 301 within the air duct component 307. Similar to those described above, examples of the randomized motion may include, but are not limited to, a left movement motion, a right movement motion, a front movement motion, a back movement motion, an up movement motion, a down movement motion, a rotating motion, a swinging motion, and/or the like.

As illustrated in FIG. 3B, the gas detection component 301 may be suspended or hanged within the air duct component 307 through the suspension connector component 303. In some embodiments, the air duct component 307 receives a gas flow associated with gaseous substance. In some embodiments, the gas detection component 301 is immersed in the gas flow and exposed to the gaseous substance. In some embodiments, the gaseous substance from the gas flow exerts aerodynamic force on the surface of the asymmetrical outer housing 311 of the gas detection component 301. Because the asymmetrical outer housing 311 is in an asymmetrical shape, the force exerted on different portions of the asymmetrical outer housing 311 by the gas flow are different, therefore creating asymmetrical aerodynamic forces on the asymmetrical outer housing 311. Because the gas detection component 301 is suspended within the air duct component 307 through the suspension connector component 303, the asymmetrical aerodynamic forces cause a randomized motion of the gas detection component 301. As such, the asymmetrical outer housing 311 of the gas detection component 301 enables the gas flow within the air duct component 307 to cause the randomized motion of the gas detection component 301 within the air duct component 307, providing various technical benefits and advantages.

For example, one of the technical challenges and difficulties associated with gas detection in air duct components is the lack of sufficient sampling contact with the gaseous substance in the gas flow as described above. Because of the randomized motion of the gas detection component 301 within the air duct component 307, the gas detection component 301 may sample gaseous substances in different locations on the cross section of the air duct component 307. Therefore, various embodiments of the present disclosure can increase the sampling contacts between the gas sensors in the gas detection component 301 and gaseous substance that are in the gas flow in the air duct component 307, and provide more accurate detection results of gaseous substances in the air duct component 307.

Additionally, the randomized motion of the gas detection component 301 is caused by the gas flow within the air duct component 307. As such, various embodiments of the present disclosure can increase the sampling contacts of the gas sensors in the gas detection component 301 and gaseous substance in the air duct component 307 without requiring duplicated gas sensors, therefore providing technical benefits such as, but not limited to, reducing the weights imposed on the air duct component, reducing the manufacturing and operation cost, and increasing the easiness and the simplicity in installing and maintaining the gas detection systems.

In some embodiments, a gas detection component weight associated with the gas detection component 301 is configurable based on a flow rate of the gas flow. For example, the gas detection component weight associated with the gas detection component 301 can be increased by adding one or more additional weight-carrying elements (such as, but not limited to, weight blocks) into the asymmetrical outer housing 311 of the example gas detection component 301, and can be reduced by removing one or more weight-carrying elements out of the asymmetrical outer housing 311 of the example gas detection component 301. In some embodiments, the higher the flow rate, the more the gas detection component weight of the gas detection component 301. The lower the flow rate, the less the gas detection component weight of the gas detection component 301. As such, by adjusting the gas detection component weight associated with the gas detection component 301 based on the flow rate of the gas flow, various embodiments of the present disclosure provide a sufficient range of motion for the gas detection component 301 to detect gaseous substances in the air duct component.

In some embodiments, the gas detection component weight associated with the gas detection component 301 is between 60 grams to 100 grams. In some embodiments, the gas detection component weight associated with the gas detection component 301 may be within other weight range(s).

Referring now to FIG. 3C, the example gas detection system 300 comprises the connector protector component 309. In some embodiments, the connector protector component 309 protects the suspension connector component 303 when the suspension connector component 303 is in motion.

In some embodiments, the connector protector component 309 comprises a tube portion 321 and a trumpet collar portion 313 connected to the tube portion 321.

In some embodiments, the tube portion 321 of the connector protector component 309 is in a shape similar to a tube or a conduit. In some embodiments, the tube portion 321 of the connector protector component 309 may comprise a cable gland. In some embodiments, at least a portion of the suspension connector component 303 passes through the tube portion 321 of the connector protector component 309. For example, the tube portion 321 of the connector protector component 309 comprises a central opening, and at least a portion of the suspension connector component 303 may pass through the central opening.

Similar to those described above, the air duct component 307 may comprise an air duct wall 315 and defines an air duct opening 317 on the air duct wall 315. In some embodiments, the tube portion 321 of the connector protector component 309 is positioned through the air duct opening 317. As the suspension connector component 303 passes through the tube portion 321 of the connector protector component 309, the suspension connector component 303 passes through the air duct opening 317 of the air duct wall 315 so that a first end of the suspension connector component 303 is connected to the gas detection component 301 (that is suspected within the air duct component 307) and a second end of the suspension connector component 303 is connected to the data transmitter component 305 (that is positioned out of the air duct component 307).

In some embodiments, the tube portion 321 of the connector protector component 309 provides an intrinsically safe barrier between the suspension connector component 303 and the air duct wall 315 of the air duct component 307. For example, the intrinsically safe barrier of the tube portion 321 can limit the voltage and/or the current from the suspension connector component 303.

In some embodiments, the connector protector component 309 further comprises a seal plate 319. In some embodiments, the tube portion 321 of the connector protector component 309 is also positioned through the seal plate 319. In some embodiments, the seal plate 319 is positioned on the air duct wall 315 to cover the air duct opening 317. As such, the seal plate 319 may seal the air duct opening 317 and prevent the gaseous substance in the air duct component 307 from flowing out of the air duct component 307.

In the example shown in FIG. 3C, the trumpet collar portion 313 of the connector protector component 309 is positioned within the air duct component 307. In some embodiments, the trumpet collar portion 313 of the connector protector component 309 corresponds to a flared portion of the connector protector component 309. As described above, the suspension connector component 303 may pass through the tube portion 321 of the connector protector component 309 and suspend the gas detection component 301 within the air duct component 307. As described above, the gas flow in the air duct component 307 may cause randomized motions of the gas detection component 301 (for example, randomized movement motions, randomized swinging motions, randomized rotation motions, and/or the like as described above). In some embodiments, the randomized motion of the gas detection component 501 causes the suspension connector component 303 to contact a trumpet collar inner surface of the trumpet collar portion 313 without contacting an air duct inner surface of the air duct wall 315 of the air duct component 307. In other words, the trumpet collar portion 313 of the connector protector component 309 can protect the suspension connector component 303 from being torn or cut by friction against the edges of the air duct opening 317 on the air duct wall 315. Additionally, or alternatively, the trumpet collar portion 313 can prevent extreme folding of the suspension connector component 303.

While the description above provides an example of a connector protector component, it is noted that the scope of the present disclosure is not limited to the description above. In some examples, an example connector protector component may comprise one or more additional and/or alternative elements. For example, an example connector protector component may comprise a bayonet lock that secures the example connector protector component to the air duct component and a glued bracket where the example suspension connector component may pass through.

Figure 4:
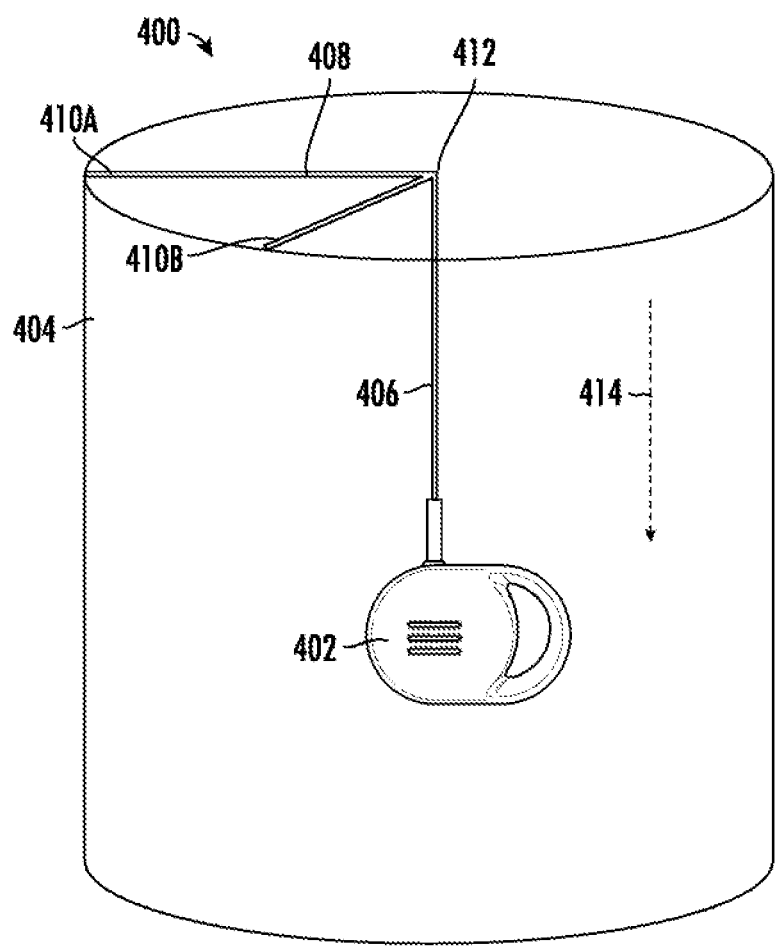
FIG. 4 illustrates an example view of an example gas detection component that is suspended within an example air duct component by an example suspension connector component in accordance with some embodiments of the present disclosure.

Referring now to FIG. 4, an example view 400 illustrates an example gas detection component 402 that is suspended within an example air duct component 404 by a suspension connector component 406 in accordance with some embodiments of the present disclosure.

Similar to those examples described above, the air duct component 404 receives a gas flow associated with gaseous substances. In the example view 400, the flow direction of the gas flow in the air duct component 404 is shown by the arrow 414.

FIG. 3A to FIG. 3C above illustrate examples where the gaseous substance flows horizontally in the air duct component 307 (e.g. the flow direction of the gaseous substance is orthogonal to the direction of the gravity's pull on the suspension connector component 303 and the gas detection component 301). As such, the suspension connector component 303 is orthogonal to the flow direction of the gas flow of the gaseous substance in the air duct component 307 (e.g. orthogonal to the central axis of the air duct component 307).

In contrast, the example view 400 shown in FIG. 4 illustrates an example where the gaseous substance flows vertically in the air duct component 404 (e.g. the flow direction of the gaseous substance is parallel to the direction of the gravity's pull on the suspension connector component 406 and the gas detection component 402). As such, the suspension connector component 406 is in a parallel arrangement with the flow direction of the gas flow of the gaseous substance in the air duct component 404 as shown by the arrow 414. In other words, the suspension connector component 406 is parallel to the central axis of the air duct component 404.

In some embodiments, a first end of the suspension connector component 406 is connected to the gas detection component 402, similar to those described above in connection with at least FIG. 1A to FIG. 1C and FIG. 3A to FIG. 3C. In some embodiments, a second end of the suspension connector component 406 is secured to a connection point 412 of the suspension support rack 408.

In some embodiments, the suspension support rack 408 may comprise rigid material such as, but not limited to, metal. In some embodiments, the rigid material of the suspension support rack 408 enables structural support for the suspension connector component 406 and the gas detection component 402.

In some embodiments, the suspension support rack 408 comprises a first leg portion 410A and a second leg portion 410B. In some embodiments, the first leg portion 410A comprises a first end and a second end, and the second leg portion 410B comprises a first end and a second end.

For example, the first end of the first leg portion 410A is fastened to a first point on the periphery of the air duct component edge of the air duct component 404, and the first end of the second leg portion 410B is fastened to a second point on the periphery of the air duct component edge of the air duct component 404. In the example shown in FIG. 4, the second end of the first leg portion 410A and the second end of the second leg portion 410B are fastened to one another at the connection point 412.

In some embodiments, the connection point 412 is positioned at the central point or at an approximately central point of the air duct component 404. Because the gas detection component 402 is secured to the connection point 412, the gas detection component 402 is positioned at the central point or at an approximately central point of the air duct component 404. As described above, the central point of the air duct component 404 is where the flow rate of the gaseous substance is the highest. As such, by suspending or hanging the gas detection component 402 at the central point or at the approximately central point of the air duct component 404, the gas detection component 402 can detect gaseous substance flowing at a high flow rate, therefore providing various technical benefits and advantages such as, but not limited to, increasing sampling contact between gas detection component 301 and the gaseous substance in the gas flow.

Figure 5:
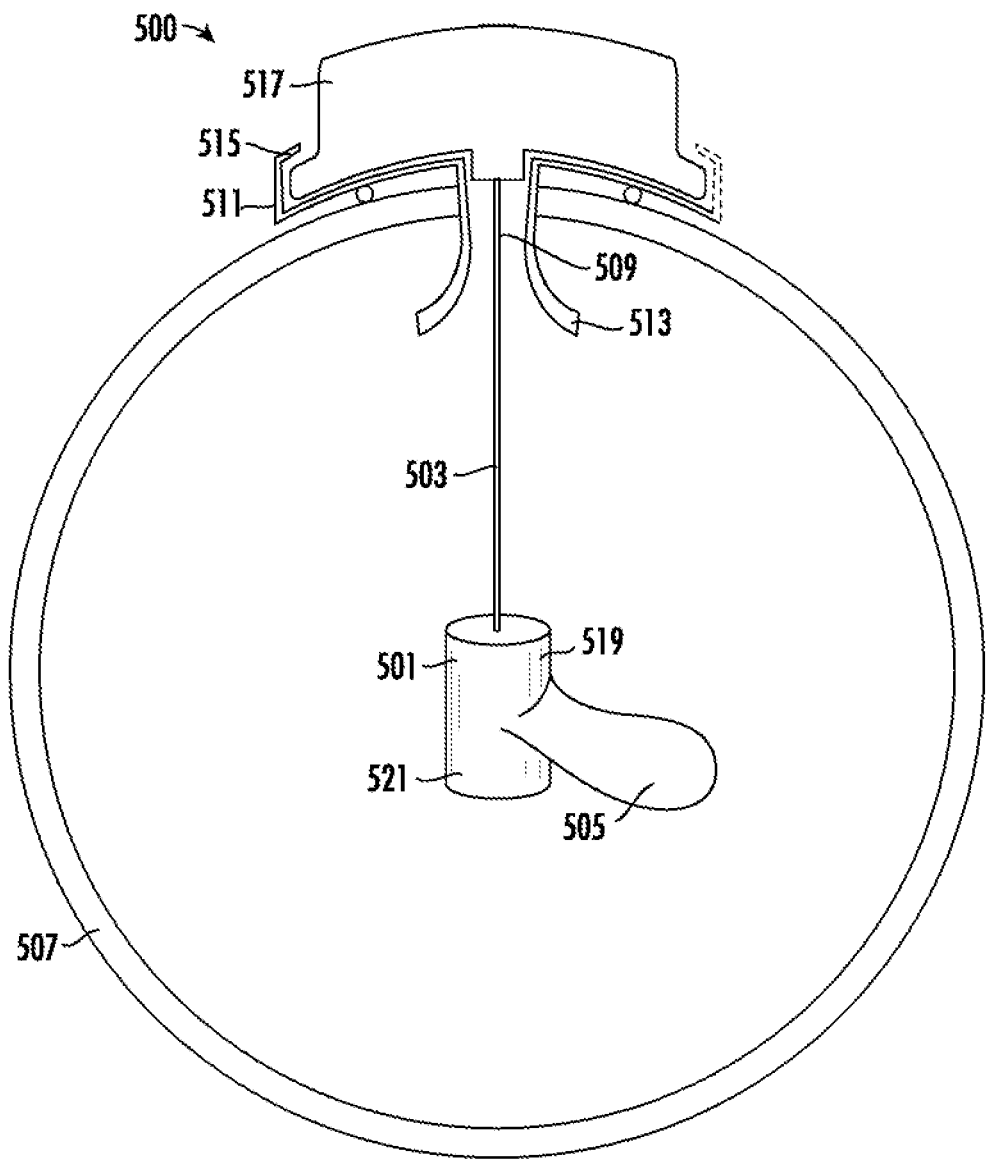
FIG. 5 illustrates an example view of an example gas detection component that is suspended within an example air duct component by an example suspension connector component in accordance with some embodiments of the present disclosure.

Referring now to FIG. 5, an example view 500 illustrates an example gas detection component 501 that is suspended within an example air duct component 507 by an example suspension connector component 503 in accordance with some embodiments of the present disclosure.

In some embodiments, the example gas detection component 501 comprises an asymmetrical outer housing 519 that is in an asymmetrical shape. For example, the asymmetrical outer housing 519 comprises a cylindrical portion 521 and at least one wing portion 505.

In some embodiments, the cylindrical portion 521 is in a shape similar to a cylindrical shape. In some embodiments, the at least one wing portion 505 is in a shape similar to a blade from a propeller (or similar to the shape of a maple seed). In some embodiments, the at least one wing portion 505 extends from an outer surface of the cylindrical portion 521 of the asymmetrical outer housing 519, creating the asymmetrical shape of the asymmetrical outer housing 519.

In some embodiments, the at least one wing portion 505 is immersed in the gas flow and exposed to the gaseous substance in the air duct component 507. For example, the at least one wing portion 505 comprises a front wing surface and a back wing surface that is opposite to the front wing surface. In some embodiments, the front wing surface of the at least one wing portion 505 may correspond to a front surface of the at least one wing portion 505 where the gaseous substances may flow onto. The back wing surface of the at least one wing portion 505 may correspond to a back surface of the at least one wing portion 505 where the gaseous substances may flow from.

In some embodiments, the gas flow of the gaseous substance in the air duct component 507 pushes the front surface of the at least one wing portion 505. In particular, the gaseous substance from the gas flow exerts aerodynamic force on the at least one wing portion 505 of the asymmetrical outer housing 519 of the gas detection component 501, as well as on the cylindrical portion 521 of the asymmetrical outer housing 519. In some embodiments, the at least one wing portion 505 creates instability in the aerodynamics of the gas flow. As such, the force exerted on different portions of the asymmetrical outer housing 519 by the gas flow are different, creating asymmetrical aerodynamic forces on the asymmetrical outer housing 519. Because the at least one wing portion 505 is in a shape similar to a blade from a propeller, the aerodynamic force exerted on the at least one wing portion 505 may further cause the gas detection component 501 to rotate, swing, and move. As such, the at least one wing portion 505 of the gas detection component 501 enables the gas flow within the air duct component to cause the randomized motion of the gas detection component 501 within the air duct component.

As described above, one of the technical challenges and difficulties associated with gas detection in air duct components is the lack of sufficient sampling contact with the gaseous substance in the gas flow. Because of the randomized motion of the gas detection component 501 within the air duct component 507, the gas detection component 501 may sample gaseous substances in different locations on the cross section of the air duct component 507. Therefore, various embodiments of the present disclosure can increase sampling contacts between the gas sensors and gaseous substance, and provide more accurate detection results of gaseous substance in the air duct component.

Additionally, the randomized motion of the gas detection component 501 is caused by the gas flow within the air duct component 507. As such, various embodiments of the present disclosure can increase sampling contacts of the gas sensors and gaseous substance without requiring duplicated gas sensors, therefore providing technical benefits such as, but not limited to, reducing the weights imposed on the air duct component, reducing the manufacturing and operation cost, and increase the easiness and the simplicity in installing and maintaining the gas detection systems.

In the example shown in FIG. 5, the air duct component 507 comprises an air duct opening 509 on the air duct wall of the air duct component 507. In some embodiments, a connector protector component 511 is positioned through the air duct opening 509.

For example, the connector protector component 511 comprises a trumpet collar portion 513 and a locking portion 515. In some embodiments, the locking portion 515 is connected to the trumpet collar portion 513. In some embodiments, the locking portion 515 and the trumpet collar portion 513 define a central opening.

In some embodiments, the locking portion 515 may comprise one or more locking mechanisms for securing a base component 517 on top of the locking portion 515. In some embodiments, a second end of the suspension connector component 503 is secured to the base component 517. In some embodiments, at least a portion of the suspension connector component 503 passes through the central opening defined by the trumpet collar portion 513 and the locking portion 515 of the connector protector component 511 as shown in FIG. 5.

In some embodiments, the trumpet collar portion 513 of the connector protector component 511 passes through the air duct opening 509 and extends into the air duct component 507. In some embodiments, the trumpet collar portion 513 of the connector protector component 511 corresponds to a flared portion of the connector protector component 511. As described above, the suspension connector component 503 may pass through the central opening defined by the trumpet collar portion 513 and the locking portion 515 of the connector protector component 511, and may suspend the gas detection component 501 within the air duct component 507. As described above, the gas flow in the air duct component 507 may cause randomized motions of the gas detection component 501 (for example, randomized movement motions, randomized swinging motions, randomized rotation motions, and/or the like as described above). In some embodiments, the randomized motion of the gas detection component 501 causes the suspension connector component 503 to contact a trumpet collar inner surface of the trumpet collar portion 513 without contacting an air duct inner surface of the air duct wall of the air duct component 507. In other words, the trumpet collar portion 513 of the connector protector component 511 can protect the suspension connector component 503 from being torn or cut by friction against the edges of the air duct opening 509 on the air duct wall of the air duct component 507. Additionally, or alternatively, the trumpet collar portion 513 can prevent extreme folding of the suspension connector component 503.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

The invention claimed is:

1. An apparatus for gas detection in an air duct component that receives a gas flow associated with gaseous substance, the apparatus comprising:
 a suspension connector component comprising a first end connected to a gas detection component that is suspended within the air duct component; and
 the gas detection component comprising an asymmetrical outer housing so that the gas flow causes a randomized motion of the gas detection component within the air duct component.

2. The apparatus of claim 1, wherein the gas detection component is suspended at a central point of the air duct component.

3. The apparatus of claim 1, wherein the gas detection component is suspended at an approximately central point of the air duct component.

4. The apparatus of claim 1, wherein the suspension connector component defines a suspension axis, wherein the asymmetrical outer housing of the gas detection component is asymmetrical along the suspension axis.

5. The apparatus of claim 4, wherein the asymmetrical outer housing comprises a left outer housing portion and a right outer housing portion divided by the suspension axis.

6. The apparatus of claim 5, wherein the right outer housing portion is larger than the left outer housing portion.

7. The apparatus of claim 5, wherein the right outer housing portion comprises a handle element, wherein the left outer housing portion does not comprise the handle element.

8. The apparatus of claim 1, wherein a gas detection component weight associated with the gas detection component is configurable configured based on a flow rate of the gas flow.

9. The apparatus of claim 1, wherein the asymmetrical outer housing of the gas detection component comprises a front outer housing surface and a back outer housing surface, wherein the front outer housing surface is opposite to the back outer housing surface.

10. The apparatus of claim 9, wherein the asymmetrical outer housing of the gas detection component defines at least one front flow opening on the front outer housing surface and at least one back flow opening on the back outer housing surface, wherein the gaseous substance flows through the at least one front flow opening and the at least one back flow opening.

11. The apparatus of claim 1, wherein the suspension connector component comprises a second end connected to a data transmitter component that is positioned outside the air duct component.

12. The apparatus of claim 11, wherein the suspension connector component comprises at least one suspension rope and at least one electrical wiring connecting the data transmitter component and the gas detection component.

13. The apparatus of claim 12, wherein the at least one electrical wiring comprises at least one power cable and at least one data cable.

14. The apparatus of claim 13, wherein the gas detection component is devoid of a power source.

15. The apparatus of claim 1, further comprising a connector protector component comprising a tube portion and a trumpet collar portion connected to the tube portion.

16. The apparatus of claim 15, wherein the air duct component comprises an air duct wall and defines an air duct opening on the air duct wall, wherein the tube portion of the connector protector component is positioned through the air duct opening.

17. The apparatus of claim 16, wherein at least a portion of the suspension connector component passes through the tube portion of the connector protector component.

18. The apparatus of claim 15, wherein the trumpet collar portion of the connector protector component is positioned within the air duct component.

19. The apparatus of claim 18, wherein the randomized motion of the gas detection component causes the suspension connector component to contact a trumpet collar inner surface of the trumpet collar portion without contacting an air duct inner surface of the air duct component.

\* \* \* \* \*